United States Patent
Lai et al.

(10) Patent No.: US 10,781,165 B2
(45) Date of Patent: Sep. 22, 2020

(54) PH-RESPONSIVE AMPHOTERIC SURFACTANT N-LAURYL-(α-ALKYL)-β-AMINOPROPIONIC ACID AND PREPARATION METHOD AND USES THEREOF

(71) Applicant: Shaanxi University of Science & Technology, Xi'an, Shaanxi (CN)

(72) Inventors: Xiaojuan Lai, Shaanxi (CN); Zhiqiang Dang, Shaanxi (CN); Lei Wang, Shaanxi (CN); Shaoyun Ma, Shaanxi (CN); Xianwen Li, Shaanxi (CN); Wei Tian, Shaanxi (CN); Xingen Feng, Shaanxi (CN); Yinyin Zhang, Shaanxi (CN); Xu Yang, Shaanxi (CN)

(73) Assignee: Shaanxi University of Science & Technology, Xi'an (CN)

( * ) Notice: Subject to any disclaimer, the term of this patent is extended or adjusted under 35 U.S.C. 154(b) by 0 days.

(21) Appl. No.: 16/443,898

(22) Filed: Jun. 18, 2019

(65) Prior Publication Data

US 2019/0388858 A1    Dec. 26, 2019

(30) Foreign Application Priority Data

Jun. 22, 2018  (CN) .......................... 2018 1 0650767

(51) Int. Cl.
*C07C 227/18*  (2006.01)
*B01F 17/00*   (2006.01)
(Continued)

(52) U.S. Cl.
CPC ........ *C07C 227/18* (2013.01); *B01F 17/0042* (2013.01); *C07C 227/40* (2013.01); *C07C 229/12* (2013.01)

(58) Field of Classification Search
CPC ... C07C 227/18; C07C 227/40; C07C 229/12; B01F 17/0042
See application file for complete search history.

(56) References Cited

U.S. PATENT DOCUMENTS

| 3,133,816 A | * | 5/1964 | Ben-Ezra | ................. | G03C 1/38 430/635 |
| 4,049,556 A | * | 9/1977 | Tujimoto | ............. | A62D 1/0085 252/3 |
| 5,922,909 A | * | 7/1999 | Joffre | .................... | C07C 227/06 562/553 |

FOREIGN PATENT DOCUMENTS

| CN | 102534060 | * | 7/2012 | ........... C07C 227/18 |
| JP | S48-039006 | * | 11/1973 | |

OTHER PUBLICATIONS

JP S48-039006 (JP0733909), Arai, A. et al., Non foamy detergent composition, English translation, 3 pages (Year: 1973).*
(Continued)

*Primary Examiner* — Yate' K Cutliff
(74) *Attorney, Agent, or Firm* — Wayne & Ken, LLC; Tony Hom (57) ABSTRACT

Disclosed are a pH-responsive amphoteric surfactant N-lauryl-(α-alkyl)-β-aminopropionic acid and a preparation method and uses thereof. An alkylamine and a solvent are added to a three-necked flask, stirred for complete dissolution, slowly dropwise added with methyl α-alkyl-acrylate and reacted at room temperature after the ice-water bath is removed. The reaction mixture is refluxed in water bath and evaporated under rotation to remove the solvent and the residual methyl α-alkyl-acrylate to give N-lauryl-(α-alkyl)-β-aminopropionic acid. Then N-lauryl-(α-alkyl)-β-aminopropionic acid and water are added to a three-necked flask, slowly dropwise added with a sodium hydroxide solution and reacted in water bath to give a crude product, which is
(Continued)

filtered and dried to give a purified surfactant sodium N-lauryl-($\alpha$-alkyl)-$\beta$-aminopropionate. This surfactant is suitable for the foamed acid system and its performance can be switched by adjusting pH due to pH sensitivity.

4 Claims, 5 Drawing Sheets

(51) Int. Cl.
*C07C 227/40* (2006.01)
*C07C 229/12* (2006.01)

(56) References Cited

OTHER PUBLICATIONS

CN 102534060, Yu, D. et al., Method for preparation of retanning fatliquor, English translation, 9 pages (Year: 2012).*
Yang,Xizoling et al.,Studies on the synthetic process of amino acids and amino acid-based surfactants.May 25, 2017.

* cited by examiner

PH-RESPONSIVE AMPHOTERIC SURFACTANT N-LAURYL-(α-ALKYL)-β-AMINOPROPIONIC ACID AND PREPARATION METHOD AND USES THEREOF

CROSS REFERENCE TO RELATED APPLICATIONS

This application claims the benefit of priority from Chinese Patent Application No. 201810650767.7, filed on Jun. 22, 2018. The content of the aforementioned application, including any intervening amendments thereto, is incorporated herein with reference in its entirety.

TECHNICAL FIELD

The application relates to surfactants, and more particularly to a pH-responsive amphoteric surfactant N-lauryl-(α-alkyl)-β-aminopropionic acid and a preparation method and uses thereof.

BACKGROUND

The foaming and defoaming of surfactants play an important role in daily life and industrial engineering. For example, the surfactant used in some products such as cosmetics and oilfield foaming agents is required to have desirable foamability, while the surfactant with poor foamability is suitable for products such as defoamer and detergent. Moreover, in some fields, the surfactant with an adjustable foamability is desired, that is, the surfactant can be adjusted to exhibit foamability or defoamability as required. For example, in a foamed acid system, the surfactant is required to maintain a good foamability during the acidification, and is required to have a desirable defoamability after the acid fracturing is completed and the acid fluid is flowed back to the ground to facilitate the treatment of the solid residues carried by the flowback system. In this case, there is a need to develop a novel surfactant, i.e., a stimuli-responsive surfactant, which can be reversibly adjusted to have the original property by adding an appropriate amount of a base to the flowback system in the cycle.

Recently, various stimuli-responsive or switchable surfactants have been developed, which are triggered by the factors including pH, temperature, oxidation-reduction, light, magnetism and $CO_2/N_2$. For example, Xiaoling Yang et al. synthesized a pH-responsive surfactant sodium lauroyl glutamate through a three-step reaction by using lauric acid, phosphorus trichloride and sodium amino acid as raw materials. In the synthesis process, lauric acid was first reacted with phosphorus trichloride; after the reaction was completed, the upper-layer product was separated and distilled under vacuum to give a lauroyl chloride distillate at 134-137° C. (1.467 KPa); and the lauroyl chloride distillate was then reacted with the sodium amino acid to synthesize a crude sodium N-lauroyl amino acid which was purified by acidification, filtration under vacuum, washing with water and petroleum ether, recrystallization, etc., and subsequently neutralized with a sodium hydroxide solution to produce the final product sodium N-lauroyl amino acid. However, this method involves some obvious defects such as the difficulty in control, complicated operation and excessive by-products.

SUMMARY

An object of the application is to provide a pH-responsive amphoteric surfactant N-lauryl-(α-alkyl)-β-aminopropionic acid and a preparation method and uses thereof. The pH-responsive amphoteric surfactant of the invention is suitable for the preparation of a stimuli-responsive foamed acid system.

The technical solutions of the application are described below.

A method for preparing a pH-responsive amphoteric surfactant N-lauryl-(α-alkyl)-β-aminopropionic acid comprises steps of:

step (1) adding 40-60 parts by weight of an alkylamine and 20-100 parts by weight of a solvent to a three-necked flask and stirring until they are completely dissolved; placing the three-necked flask in an ice water bath and slowly dropwise adding 25-30 parts by weight of methyl α-alkyl-acrylate to the three-necked flask under stirring; removing the ice water bath and reacting the reaction mixture at room temperature for 4-8 h and then at 70-90° C. in a water bath under reflux for 3-6 h; transferring the reaction mixture to a rotary evaporator to remove the solvent and the residual methyl α-alkyl-acrylate to produce N-lauryl-(α-alkyl)-β-aminopropionic acid; and step (2) adding the N-lauryl-(α-alkyl)-β-aminopropionic acid prepared in step (1) and 50-150 parts by weight of water to a three-necked flask; preparing 10-15 parts by weight of sodium hydroxide into a sodium hydroxide solution with a mass fraction of 10%-20%; heating a water bath to 60-80° C. and slowly dropwise adding the sodium hydroxide solution to the three-necked flask to fully saponify the N-lauryl-(α-alkyl)-β-aminopropionic acid; reacting the reaction mixture at 60-70° C. in the water bath for 2-10 h and then at 80-90° C. in the water bath for 2-5 h to produce a crude product; drying the crude product to remove water; dissolving the dried crude product with ethanol followed by filtration to remove the sodium hydroxide while the solution of the dried crude product in ethanol is hot; and drying to produce the amphoteric surfactant sodium N-lauryl-(α-alkyl)-β-aminopropionate.

In an embodiment, the alkylamine is selected from the group consisting of dodecylamine, tetradecylamine, hexadecylamine and octadecylamine.

In an embodiment, the solvent is selected from the group consisting of methanol, ethanol and isopropanol.

In an embodiment, the methyl α-alkyl-acrylate has the following structural formula:

wherein $R_2$ is an alkyl having 1-3 carbon atoms.

A pH-responsive amphoteric surfactant N-lauryl-(α-alkyl)-β-aminopropionic acid prepared by the above method has a general formula shown as follows:

wherein $R_1$ is a long-chain alkyl group having 12-18 carbon atoms; and $R_2$ is an alkyl having 1-3 carbon atoms.

In an embodiment, under an acidic condition, the pH-responsive amphoteric surfactant N-lauryl-(α-alkyl)-β-aminopropionic acid has a structural formula shown as follows:

In an embodiment, under a basic condition, the pH-responsive amphoteric surfactant N-lauryl-(α-alkyl)-β-aminopropionic acid has a structural formula shown as follows:

In an embodiment, the pH-responsive amphoteric surfactant N-lauryl-(α-alkyl)-β-aminopropionic acid at its isoelectric point has a structural formula shown as follows:

A use of the pH-responsive amphoteric surfactant N-lauryl-(α-alkyl)-β-aminopropionic acid comprises a step of:

using 0.3 wt. %-0.5 wt. % of the pH-responsive amphoteric surfactant N-lauryl-(α-alkyl)-β-aminopropionic acid, based on the weight of an aqueous phase.

In an embodiment, the pH-responsive amphoteric surfactant N-lauryl-(α-alkyl)-β-aminopropionic acid has a surface activity at a pH lower than 7 and loses the surface activity at a pH greater than 7; and a foamed acid system is pH-responsive when added with the pH-responsive amphoteric surfactant N-lauryl-(α-alkyl)-β-aminopropionic acid as a foaming agent; when the pH of the foamed acid system is lower than 7, the system shows high foamability and good foam stability, and when the foam is returned from the wellbore to the ground, a base is introduced to make pH greater than 7 to defoam the foamed acid system; solid impurities carried in the foamed acid system are separated; and this process is repeated.

The application has the following beneficial effects.

The pH-responsive amphoteric surfactant N-lauryl-(α-alkyl)-β-aminopropionic acid of the invention is suitable for the preparation of a foamed acid system. Performances of the pH-sensitive surfactant and the foamed acid system containing the same can be switched by adjusting the pH from a value lower than 7 to a value greater than 7. This pH-responsive surfactant is synthesized by commercially available alkylamine and methyl α-alkyl-acrylate, and the process is simple and easy to operate, and avoids the synthesis of a complex switchable surfactant, thereby having a great application value.

DETAILED DESCRIPTION OF EMBODIMENTS

Figure 1:
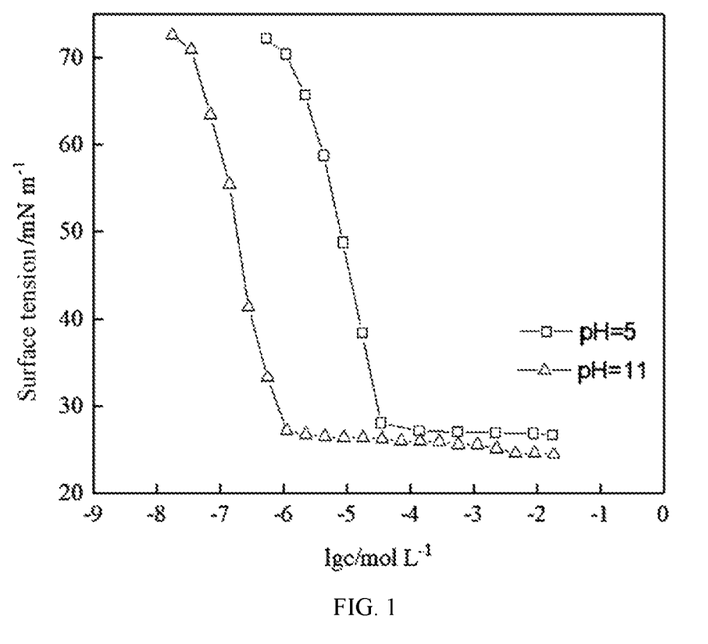
FIG. 1 is a graph showing surface tensions at different pHs versus concentrations of a surfactant prepared in Example 1.
Figure 2:
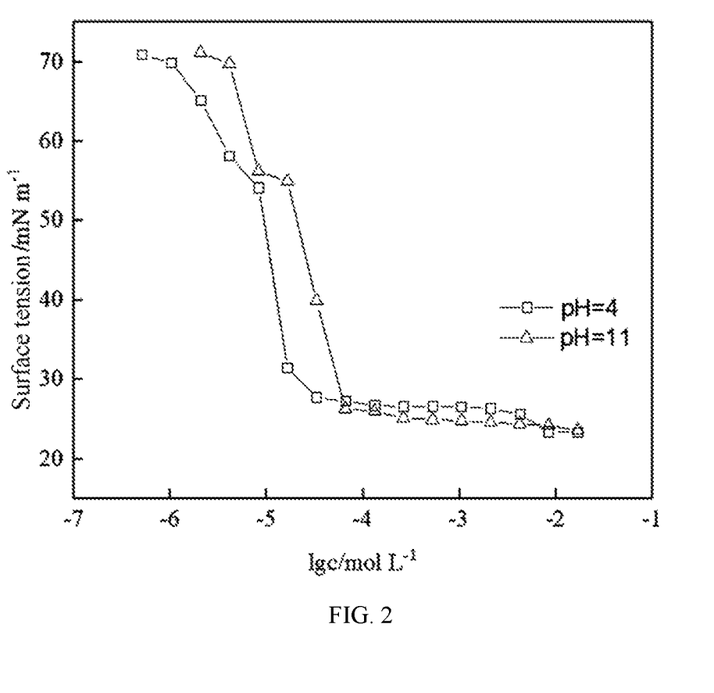
FIG. 2 is a graph showing surface tensions at different pHs versus concentrations of a surfactant prepared in Example 2.
Figure 3:
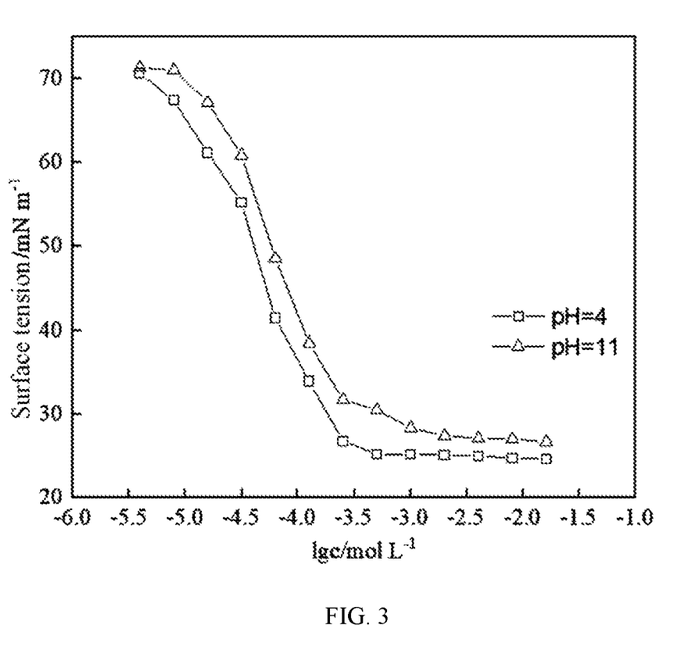
FIG. 3 is a graph showing surface tensions at different pHs versus concentrations of a surfactant prepared in Example 3.
Figure 4:
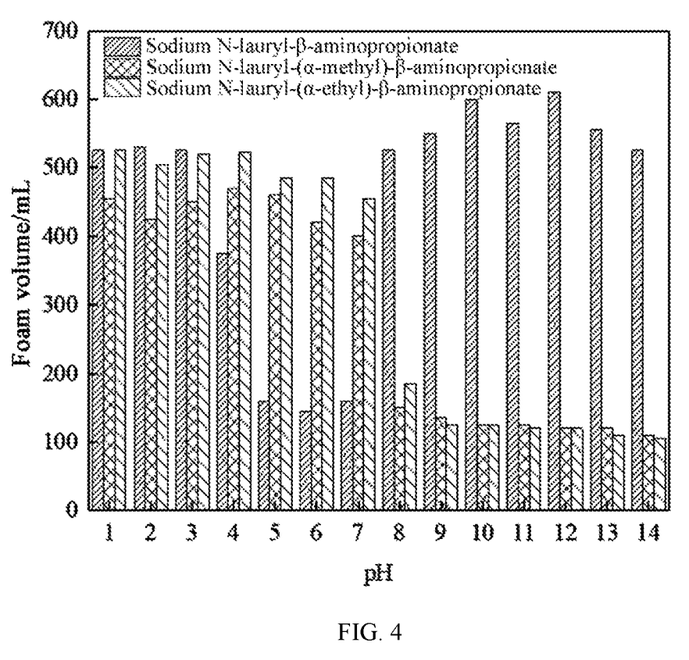
FIG. 4 is a graph showing volumes of foams generated by the surfactants prepared in Examples 1-3 versus pH.
Figure 5:
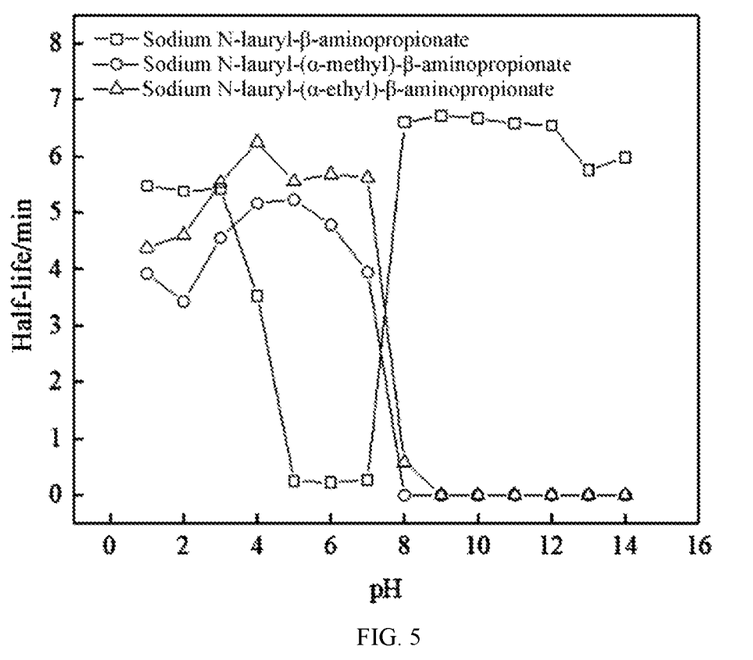
FIG. 5 is a graph showing half-life of the surfactants prepared in Examples 1-3 versus pH.

The application will be described in detail with reference to the following embodiments.

The invention attempts to replace the methyl acrylate with a methyl acrylate bearing an α-alkyl to produce a surfactant suitable for the foamed acid system, where the methyl acrylate bearing an α-alkyl includes methyl methacrylate and methyl ethacrylate. Such amphoteric surfactant molecules contain both a cationic group (amino group) and an anionic group (carboxyl group), and the type of charges carried by such molecules is associated with the pH of the medium. At the isoelectric point or in the isoelectric range, the cationic group and the anionic group carry positive and negative charges, respectively, so that the molecule is electrically neutral. In this case, since the hydrophilic groups (amino cation and carboxyl anion) fail to form an inner salt due to the steric hindrance effect generated by the α-alkyl, the surface activity is maintained. In addition, the surface activity is even improved due to the enhanced hydrophilicity. At a pH lower than the isoelectric point or range, since the cationic group is positively charged and the anionic group is uncharged, the molecule is positively charged (positively-charged amino). At this time, the surfactant still has a good surface activity due to the improved solubility. While at a pH greater than the isoelectric point or range, since the anionic group is negatively charged and the cationic group is uncharged, the molecule is negatively charged. In this case, the adsorption of carboxylate ions on the surface of the solution is greatly reduced due to the steric hindrance effect generated by the α-alkyl, thereby lowering the surface activity and making it difficult to foam. Therefore, a stimuli-responsive amphoteric surfactant, which shows a rapid response to the pH change in the range of pH<7 and pH>7, is prepared, facilitating the application of related technology.

The invention provides a method for preparing a pH-responsive amphoteric surfactant N-lauryl-(α-alkyl)-β-aminopropionic acid, including steps of:

Step (1) Preparation of
N-lauryl-(α-alkyl)-β-aminopropionic Acid adding 40-60 parts by weight of an alkylamine and 20-100 parts by weight of a solvent to a three-necked flask and stirring until they are completely dissolved; placing the three-necked flask in an ice water bath and slowly dropwise adding 25-30 parts by weight of methyl α-alkyl-acrylate to the three-necked flask under stirring; removing the ice water bath and reacting the reaction mixture at room temperature for 4-8 h and then at 70-90° C. in a water bath under reflux for 3-6 h; transferring the reaction mixture to a rotary evaporator to remove the solvent and the residual methyl α-alkyl-acrylate to produce N-lauryl-(α-alkyl)-β-aminopropionic acid; and

Step (2) Preparation of Sodium N-lauryl-(α-alkyl)-β-aminopropionate adding the N-lauryl-(α-alkyl)-β-aminopropionic acid prepared in step (1) and 50-150 parts by weight of water to a three-necked flask; preparing 10-15 parts by weight of sodium hydroxide into a sodium hydroxide solution with a mass fraction of 10%-20%; heating a water bath to 60-80° C. and slowly dropwise adding the sodium hydroxide solution to the three-necked flask to fully saponify the N-lauryl-(α-alkyl)-β-aminopropionic acid; reacting the reaction mixture at 60-70° C. in the water bath for 2-10 h and then at 80-90° C. in the water bath for 2-5 h to produce a crude product; drying the crude product to remove water; dissolving the dried crude product with ethanol followed by filtration to remove the sodium hydroxide while the solution of the dried crude product in ethanol is hot; and drying to produce the amphoteric surfactant sodium N-lauryl-(α-alkyl)-β-aminopropionate.

The alkylamine is a single long-chain alkylamine or a double long-chain alkylamine, where the long-chain alkyl has 12-18 carbon atoms. The alkylamine is selected from the group consisting of dodecylamine, tetradecylamine, hexadecylamine and octadecylamine.

The solvent is selected from the group consisting of methanol, ethanol and isopropanol.

The methyl α-alkyl-acrylate has the following structural formula:

where $R_2$ is an alkyl having 1-3 carbon atoms.

The pH-responsive amphoteric surfactant N-lauryl-(α-alkyl)-β-aminopropionic acid prepared by the above method has a general formula shown as follows:

where $R_1$ is a long-chain alkyl group having 12-18 carbon atoms; and $R_2$ is an alkyl having 1-3 carbon atoms.

Under an acidic condition, the pH-responsive amphoteric surfactant N-lauryl-(α-alkyl)-β-aminopropionic acid has a structural formula shown as follows:

Under a basic condition, the pH-responsive amphoteric surfactant N-lauryl-(α-alkyl)-β-aminopropionic acid has a structural formula shown as follows:

The pH-responsive amphoteric surfactant N-lauryl-(α-alkyl)-β-aminopropionic acid at its isoelectric point has a structural formula shown as follows:

The pH-responsive amphoteric surfactant N-lauryl-(α-alkyl)-β-aminopropionic acid is used at a mass fraction of 0.3%-0.5% based on the weight of an aqueous phase, preferably 0.5%.

The pH-responsive amphoteric surfactant N-lauryl-(α-alkyl)-β-aminopropionic acid has a surface activity at a pH lower than 7 and loses the surface activity at a pH greater than 7.

A foamed acid system is pH-responsive when added with the pH-responsive amphoteric surfactant N-lauryl-(α-alkyl)-β-aminopropionic acid as a foaming agent, when pH of the foamed acid system is lower than 7, the system shows high foamability and good foam stability, and when the foam is returned from the wellbore to the ground, a base is introduced to make pH greater than 7 to defoam the foamed acid system; solid impurities carried in the foamed acid system are separated; and this process is repeated. This process is specifically described as follows.

The amphoteric surfactant N-lauryl-(α-alkyl)-β-aminopropionic acid is first dissolved in water and adjusted with a hydrochloric acid (HCl) solution at room temperature to the pH at the isoelectric point or range, generally 3~5, to allow the system for electrical neutrality. At this time, the formation of an inner salt is inhibited due to the steric hindrance of α-alkyl, so the surfactant can still maintain a high surface activity even in the isoelectric range. With the continuous adding of HCl to the system, the hydrophilic group carboxylate ions are gradually converted into a carboxyl group as a hydrophobic chain portion, and the amino group is positively charged ($NH_2^+$), so that the surfactant still has a surface activity. Therefore, the amphoteric surfactant N-lauryl-(α-alkyl)-β-aminopropionic acid can be used as an acid surfactant in a wide pH range (pH 1-7), suitable for the preparation of a foamed acid system. Then, the system is added with a base (NaOH) solution to elevate the pH to be greater than the isoelectric point or range, i.e., pH>7, so that the system is converted to be negatively charged ($COO^-$). In this case, it is difficult for the hydrophilic group ($COO^-$) to arrange closely at the surface of the solution or in the molecular aggregates due to the steric hindrance of α-alkyl, so that the adsorption amount is reduced and the surface activity is lost, thereby allowing the foamed acid system to be rapidly defoamed. When the pH is lowered again by acidification, with the increase of adsorption amount of the hydrophilic group, the foamability of the surfactant is gradually improved, allowing the foamed acid system for good foamability and foam stability again. The stimuli-responsive surfactant triggered by pH and the foamed acid system containing the same can be switched multiple times between "with surface activity" and "without surface activity" as well as between "having foamability" and "having defoamability". The salt (NaCl) derived from the neutralization performed by adding an acid or a base does not affect the foamability of the system and can even improve the foamability in a short-term cycle.

Foamabilities of the amphoteric surfactants prepared in Examples 1-3 were subjected to laboratory evaluation according to GB/T7462-1994"Determination of Foaming Power". The half-life of the foam was used to evaluate the foam stability. A 1% (mass fraction) HCl solution and a 1% (mass fraction) NaOH solution were prepared for use.

Example 1

Step (1)

42.34 parts by weight of dodecylamine and 30 parts by weight of methanol were added to a three-necked flask equipped with a reflux-condensing unit and a stirring unit and stirred until they were completely dissolved. The three-necked flask was placed in an ice water bath and slowly dropwise added with 28.6 parts by weight of methyl acrylate under rapid stirring. Then the ice water bath was removed and the reaction mixture was reacted at room temperature for 6 h and then at 80° C. in a water bath under reflux for 4 h. The reaction mixture was evaporated under rotation to remove the solvent and the residual methyl acrylate to produce N-lauryl-β-aminopropionic acid.

Step (2)

72.42 parts by weight of N-lauryl-β-aminopropionic acid and 100 parts by weight of water were added to a three-necked flask equipped with a reflux-condensing unit and a stirring unit and stirred uniformly. A sodium hydroxide solution was prepared from 12.56 parts by weight of sodium hydroxide and 50 parts by weight of water. After a water bath was heated to 70° C., the reaction mixture was slowly dropwise added with the sodium hydroxide and reacted at 70° C. in the water bath for 6 h and then at 90° C. in the water bath for 3 h to produce a crude product. The crude product was dried to remove water, dissolved in ethanol, filtered to remove sodium hydroxide when the solution of the dried crude product in ethanol is hot, distilled under vacuum to remove ethanol and dried to finally produce the surfactant sodium N-lauryl-β-aminopropionate.

Sodium N-lauryl-β-aminopropionate was used as a comparison for the analysis of response to pH. 0.5 g of sodium N-lauryl-β-aminopropionate was added to a 200 mL bottle, added with 100 mL of distilled water and ultrasonicated by an ultrasonic disperser (JYD-650, Shanghai) at 50 W for 10 min for uniform dispersion. The volume and half-life of the foam were determined using a Waring Blender method. Specifically, the solution was adjusted to pH of 5.61 and the volume and half-life of the foam were determined, and then the solution was adjusted with a base solution to pH of about 11.27 and the determination was performed again. Such process was repeated several times.

| pH | Foam volume/mL | Half-life/s |
| --- | --- | --- |
| 11.48 | 565 | 395 |
| 5.61 | 155 | 27 |
| 11.27 | 530 | 399 |
| 5.21 | 160 | 15 |
| 11.56 | 500 | 441 |
| 6.13 | 145 | 13 |
| 11.59 | 520 | 440 |
| 7.02 | 160 | 16 |

Example 2

Step (1)

44.34 parts by weight of tetradecylamine and 25 parts by weight of methanol were added to a three-necked flask equipped with a reflux-condensing unit and a stirring unit and stirred until they were completely dissolved. The three-necked flask was placed in an ice water bath and slowly dropwise added with 26.35 parts by weight of methyl α-methacrylate under rapid stirring. Then the ice water bath was removed and the reaction mixture was reacted at room temperature for 5 h and then at 70° C. in a water bath under reflux for 4 h. The reaction mixture was evaporated under rotation to remove the solvent and the residual methyl α-methacrylate to produce N-lauryl-(α-methyl)-β-aminopropionic acid.

Step (2)

49.84 parts by weight of N-lauryl-(α-methyl)-β-aminopropionic acid and 80 parts by weight of water were added to a three-necked flask equipped with a reflux-condensing unit and a stirring unit and stirred uniformly. A sodium hydroxide solution was prepared from 7.69 parts by weight of sodium hydroxide and 20 parts by weight of water. After a water bath was heated to 60° C., the reaction mixture was slowly dropwise added with the sodium hydroxide and reacted at 70° C. in the water bath for 8 h and then at 85° C. in the water bath for 4 h to produce a crude product. The crude product was dried to remove water, dissolved in ethanol, filtered to remove sodium hydroxide when the solution of the dried crude product in ethanol is hot, distilled under vacuum to remove ethanol and dried to finally produce the surfactant sodium N-lauryl-(α-methyl)-β-aminopropionate.

Response of the sodium N-lauryl-(α-methyl)-β-aminopropionate to pH was analyzed. 0.5 g of sodium N-lauryl-(α-methyl)-β-aminopropionate was added to a 200 mL bottle, added with 100 mL of distilled water and ultrasonicated by an ultrasonic disperser (JYD-650, Shanghai) at 50 W for 10 min for uniform dispersion. The volume and half-life of the foam were determined using a Waring Blender method. The solution was adjusted to pH of 4.61 and the volume and half-life of the foam were determined, and then the solution was adjusted with a base solution to pH of about 11.28 and the determination was performed again. Such process was repeated several times.

| pH | Foam volume/mL | Half-life/s |
| --- | --- | --- |
| 11.43 | 175 | 7 |
| 4.61 | 470 | 357 |
| 11.28 | 150 | 5 |
| 4.53 | 460 | 350 |
| 11.11 | 125 | 0 |
| 5.17 | 425 | 314 |
| 11.37 | 125 | 0 |
| 6.51 | 425 | 266 |

Example 3

Step (1)

46.32 parts by weight of hexadecylamine and 20 parts by weight of methanol were added to a three-necked flask equipped with a reflux-condensing unit and a stirring unit and stirred until they were completely dissolved. The three-necked flask was placed in an ice water bath and slowly dropwise added with 22.6 parts by weight of methyl α-ethacrylate under rapid stirring. Then the ice water bath was removed and the reaction mixture was reacted at room temperature for 7 h and then at 85° C. in a water bath under reflux for 5 h. The reaction mixture was evaporated under rotation to remove the solvent and the residual methyl α-ethacrylate to produce N-lauryl-(α-ethyl)-β-aminopropionic acid.

Step (2)

55.74 parts by weight of N-lauryl-(α-ethyl)-β-aminopropionic acid and 100 parts by weight of water were added to a three-necked flask equipped with a reflux-condensing unit and a stirring unit and stirred uniformly. A sodium hydroxide solution was prepared from 8.20 parts by weight of sodium hydroxide and 20 parts by weight of water. After a water bath was heated to 65° C., the reaction mixture was slowly dropwise added with the sodium hydroxide and reacted at 65° C. in the water bath for 6 h and then at 90° C. in the water bath for 2 h to produce a crude product. The crude product was dried to remove water, dissolved in ethanol, filtered to remove sodium hydroxide when the solution of the dried crude product in ethanol is hot, distilled under vacuum to remove ethanol and dried to finally produce the surfactant sodium N-lauryl-(α-ethyl)-β-aminopropionate.

Response of the sodium N-lauryl-(α-ethyl)-β-aminopropionate to pH was analyzed. 0.5 g of sodium N-lauryl-(α-ethyl)-β-aminopropionate was added to a 200 mL bottle, added with 100 mL of distilled water and ultrasonicated by an ultrasonic disperser (JYD-650, Shanghai) at 50 W for 10 min for uniform dispersion. The volume and half-life of the foam were determined using a Waring Blender method. The solution was adjusted to pH of 4.86 and the volume and half-life of the foam were determined, and then the solution was adjusted with a base solution to pH of about 11.33 and the determination was performed again. Such process was repeated several times.

| pH | Foam volume/mL | Half-life/s |
| --- | --- | --- |
| 11.38 | 185 | 35 |
| 4.86 | 525 | 457 |
| 11.33 | 175 | 17 |
| 4.51 | 530 | 503 |
| 11.42 | 130 | 0 |
| 4.44 | 523 | 375 |
| 11.19 | 125 | 0 |
| 4.50 | 530 | 423 |

These embodiments are not intended to limit the invention. Any equivalent variations made by those skilled in the art based on the content disclosed by the invention should fall within the scope of the invention.

What is claimed is:

1. A method for preparing a pH-responsive amphoteric surfactant N-lauryl-(α-alkyl)-β-aminopropionic acid, comprising:
   (1) adding 40-60 parts by weight of an alkylamine and 20-100 parts by weight of a solvent to a three-necked flask and stirring until they are completely dissolved; placing the three-necked flask in an ice water bath and slowly dropwise adding 25-30 parts by weight of methyl α-alkyl-acrylate to the three-necked flask under stirring; removing the ice water bath and reacting the reaction mixture at room temperature for 4-8 h and then at 70-90° C. in a water bath under reflux for 3-6 h; transferring the reaction mixture to a rotary evaporator to remove the solvent and the residual methyl α-alkyl-acrylate so as to produce N-lauryl-(α-alkyl)-β-aminopropionic acid; and
   (2) adding the N-lauryl-(α-alkyl)-β-aminopropionic acid prepared in step (1) and 50-150 parts by weight of water to a three-necked flask; preparing 10-15 parts by weight of sodium hydroxide into a sodium hydroxide solution with a mass fraction of 10%-20%; heating a water bath to 60-80° C. and slowly dropwise adding the sodium hydroxide solution to the three-necked flask to fully saponify the N-lauryl-(α-alkyl)-β-aminopropionic acid; reacting the reaction mixture at 60-70° C. in the water bath for 2-10 h and then at 80-90° C. in the water bath for 2-5 h to produce a crude product; drying the crude product to remove water; dissolving the dried crude product with ethanol followed by filtration to remove the sodium hydroxide while the solution of the dried crude product in ethanol is hot; and drying to produce the amphoteric surfactant sodium N-lauryl-(α-alkyl)-β-aminopropionate.

2. The method of claim 1, wherein the alkylamine is selected from the group consisting of dodecylamine, tetradecylamine, hexadecylamine and octadecylamine.

3. The method of claim 1, wherein the solvent is selected from the group consisting of methanol, ethanol and isopropanol.

4. The method of claim 1, wherein the methyl α-alkyl-acrylate has the following structural formula:

wherein $R_2$ is an alkyl having 1-3 carbon atoms.

* * * * *